(12) United States Patent
Ensley

(10) Patent No.: US 6,572,845 B2
(45) Date of Patent: *Jun. 3, 2003

(54) RECOMBINANT HAIR TREATMENT COMPOSITIONS

(76) Inventor: Burt D. Ensley, 7 Colts Neck Dr., Newtown, PA (US) 18940

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 80 days.

(21) Appl. No.: 09/174,186

(22) Filed: Oct. 16, 1998

(65) Prior Publication Data
US 2001/0006664 A1 Jul. 5, 2001

(51) Int. Cl.[7] .................. A61K 7/075; A61K 7/06; C12N 15/85
(52) U.S. Cl. .................. 424/70.14; 514/2; 514/44; 424/401; 424/70.1; 424/78.02; 424/70.11; 435/320.1; 435/325; 435/455; 435/69.1
(58) Field of Search .................. 514/2, 44; 424/401, 424/70.1, 78.02, 70.11, 70.14, 70.51; 435/320.1, 325

(56) References Cited

U.S. PATENT DOCUMENTS

| | | | |
|---|---|---|---|
| 3,842,848 A | 10/1974 | Karjala | 132/204 |
| 4,439,417 A | 3/1984 | Matsunaga et al. | 510/127 |
| 4,465,664 A | 8/1984 | Matsunaga et al. | 424/70.14 |
| 4,495,173 A | 1/1985 | Matsunaga et al. | 424/70.14 |
| 4,542,014 A | 9/1985 | Bresak et al. | 424/70.13 |
| 4,906,460 A | 3/1990 | Kim et al. | 424/70.14 |
| 5,612,024 A | 3/1997 | Giede et al. | 424/70.11 |
| 5,641,648 A | 6/1997 | Ferrari et al. | 435/69.1 |
| 5,726,040 A | 3/1998 | Ensley et al. | 435/69.1 |

FOREIGN PATENT DOCUMENTS

| | | |
|---|---|---|
| EP | 0615745 A1 | 9/1993 |
| WO | WO 99/35243 | 1/1999 |
| WO | WO 99/45894 | 3/1999 |

OTHER PUBLICATIONS

Winter et al. "A new mutation in the type II hair cortex keratin hHb1 involved in the inherited hair disorder monilethrix", Hum. Genet. vol. 101, pp. 165–169, 1997 (month unavailable).

Winter et al., "Mutations in the hair cortex keratin hHb6 cause the inherited hair disease monilethrix", Nat. Genet., vol. 16, Aug., pp. 372–374, 1997.

Winter et al., "The region coding for the helix termination motif and the adjacent intron 6 of the human type I hair keratin gene hHa2 contains three natural, closely spaced polymorphic sites", The Journal of Investigative Dermatology, vol. 106, No. 3, Mar., pp. 544–548, 1996.

*Primary Examiner*—David Guzo
(74) *Attorney, Agent, or Firm*—Choate, Hall & Stewart; Brenda Herschbach Jarrell; C. Hunter Baker

(57) ABSTRACT

A hair treatment composition including a non naturally-occurring keratin protein in combination with a hair treatment formula is described. The protein is preferably of human origin and has not been previously cross-linked. The protein is most preferably selected from the group of soluble keratin proteins found in human hair. Preferably, the composition contains one, preferably at least two allelic variants of the protein, most preferably in substantially the same ratio at which they are found in hair of a selected individual. The individual may be selected, for example, on the basis of having appealing hair, of being the future user of the hair treatment composition of other reasons.

24 Claims, No Drawings

SEQUENCE LISTING

```
<160> NUMBER OF SEQ ID NOS:  4

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:oligonucleotide
      primer for PCR

<400> SEQUENCE: 1
cctgctaccg aggactctca gg                                                22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:oligonucleotide
      primer for PCR

<400> SEQUENCE: 2
cgatctccag gttcaggggt gt                                                22

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:oligonucleotide
      primer for PCR

<400> SEQUENCE: 3
tgcagcggaa acgtggtgg                                                    19

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:oligonucleotide
      primer for PCR

<400> SEQUENCE: 4
ctggggcagc ggatcctcca g                                                 21
```

RECOMBINANT HAIR TREATMENT COMPOSITIONS

BACKGROUND OF THE INVENTION

Human hair varies much in length, thickness and color in different individuals and among different races of mankind. A hair consists of a root, which is the part implanted in the skin, and a shaft, which is the portion projecting from the surface. The shaft of the hair consists, from within outward, of three parts: the medulla, the cortex and the cuticle. Each layer is multicellular in nature. The medulla, usually more narrow in fine hairs, is composed of rows of polyhedral cells. The cortex constitutes the chief part of the hair shaft; its cells are elongated and united to form flat, tapered fibers that contain pigment granules in dark hair and air in white hair. The cuticle consists of a single layer of flat scales that overlap one another. Exposure of the hair to sun, wind, and modern hair styling products and techniques, (e.g., shampooing, bleaching, dyeing, tinting, and shaping of hair with wave preparations), imparts significant and unwanted damage to the cuticle and cortex of the hair shaft. As damage to certain proteins present in hair accumulates, a loss in body, luster, and smooth texture results. Such damage is also reflected in poor wet and dry compatibility, increased electrostatic charging, reduced maximum tensile strength, breaking of the hair and in the poor appearance of hair styles.

The structural component of hair consists of a side by side overlapping array of intermediate filaments classified as tough and durable protein fibers present in the cytoplasm of cells that are subject to mechanical stress. Intermediate filament proteins consist of a large superfamily of proteins that share a common structural organization. These proteins contain a thin a-helical rod domain with non-helical ends, which assemble through a dimeric coiled-coil. The dimers form higher order oligomer subunits which twist and pack together to form microscopic ropes that are woven together in different ways to form a network in the cytoplasm of the cell. This network functions to connect cells to each other and is a major structural component of epithelial tissues. In humans, at least three-quarters of all intermediate filament proteins are keratins (Lane et al., *Curr. Op, in Genet. Dev.,* V. 4, pp 412–418, 1994).

Keratins are the most complex group of intermediate filament proteins. There are at least 30 keratin proteins which can be further divided into hard keratins, (hair and nail keratins), and soft keratins, (epidermal keratins) (Yu et al., *The Journal of Investigative Dermatology,* V. 101, NO. 1, Supplement, July, 1993; and Fuchs, Ann. Rev. Biochem., V. 63, pp. 345–382, 1994). Human hair keratin proteins may be distinguished from their epidermal counterparts by a relatively higher cysteine content that reflects utilization of disulfide bonds in producing a tougher, more durable structure (Yu et al., supra). All keratins can be further divided into acidic type I keratins and basic type II keratin proteins which heterodimerize to form the higher order structure common to intermediate filaments (Fuchs et al., supra). At present, there are seven known type I hair keratins (hHa1, hHa2, hHa3-I, hHa3-II, hHa4, hHa5, and hHRa1 Hair acidic keratins) (Winter et al. *Nature Genetics,* V. 16, August, pp. 372–374, 1997) and four known type II hair keratins (hHb1, hHb3, hHb5, and hHb6 Hair basic keratins) (Rogers et al., *Differentiation,* V. 61, pp. 187–194, 1997). Together with the so called minor hair keratin pairs, Hax/Hbx, the hair keratin family comprises 13 members. Keratins are expressed in the cortex of the hair shaft, (e.g., Hb1), and in the cuticle (e.g., Ha1 and two isoforms of Ha3) (Winter et al., *The Journal of Investigative Dermatology,* V. 106, NO. 3, March, pp. 544–548, 1996).

There is an astounding heterogeneity in epithelial keratin proteins expressed in different individuals. This heterogeneity results from a polymorphism of the respective epithelial keratin genes (Mischke et al., *The Journal of Investigative Dermatology,* V. 88, No. 2, February, pp. 191–197, 1987; Lane et al., supra). Furthermore, subtle allelic variation can result in gross phenotypic defects in epithelial tissue (Lane et al., supra; Winter et al., supra; Fuchs et al., supra). For example, transgenic mice expressing mutated human epidermal keratin genes exhibit a disturbed keratin network along with tissue abnormalities resembling the autosomal dominant human skin diseases, epidermolysis bullosa simplex or epidermolytic hyperkeratosis (Winter et al., supra). Without the proper intermediate filament network, epidermal cells become fragile and prone to breakage upon mechanical stress, resulting in skin blistering.

Given the heterogeneity of epidermal keratins and the effect of this heterogeneity on the appearance of the skin, it was not surprising that polymorphisms were also found to be associated with hair keratin proteins. In one example, two polymorphic loci in the cuticular hHa2 gene, were identified and shown to be inherited as Mendelian traits (Winter et al., 1997 supra). Heterogeneity in keratin proteins can have direct effects on the tensile strength, flexibility, and dynamics of the intermediate filaments, which means that even subtle heterogeneity in intermediate filament proteins can influence the external features of the hair or skin.

The use of protein materials in the formulation of modern hair care products to provide shine, strength, softness, smoothness, and good combing properties is well known. Keratin, in particular is often utilized. Because the naturally-occurring keratin is always cross-linked and cross-linked fibers are insoluble (i.e., insoluble in water), the keratin is first rendered soluble using a variety of chemical and enzymatic methods which hydrolyze the protein (U.S. Pat. No. 4,439,417; U.S. Pat. No. 4,542,014; U.S. Pat. No. 5,612,024; U.S. Pat. No. 4,465,664; U.S. Pat. No. 4,906,460; U.S. Pat. No. 3,842,848; U.S. Pat. No. 4,495,173). The starting materials can include, for example, animal hair, human hair, feather, claw, horn, hoof and scale, among which wool and feather are preferably used.

Since the keratin proteins are from a variety of natural sources they do not reflect any particular desirable hair keratin composition and since the keratin protein is hydrolyzed to its constituent amino acids, it does not maintain the structure of the keratin protein, but is merely a simple mixture of amino acids which is added to the hair treatment composition. A better hair treatment product would avoid the use of cross-linked keratins and would preferably even provide a mechanism for tailoring the product composition to the needs or desires of particular individuals.

SUMMARY OF THE INVENTION

The present invention pertains to a hair treatment or beauty composition including a non-naturally-occurring intermediate filament protein formulated as a hair treatment composition. The intermediate filament proteins are preferably of human origin and have not been previously cross-linked. The protein is most preferably selected from the group consisting of human hair keratins. The keratin protein may include at least one additional non-naturally occurring amino acid sequence moiety, the amino acid sequence moiety preferably being selected from the group consisting of a hydrophobic sequence, a hydrophilic sequence, and a cysteine-rich sequence.

In preferred embodiments of the present invention, the hair treatment composition is formulated to reproduce one or more aspects of the keratin proteins found in the hair of a selected individual. In particular, one aspect of the present invention involves the recognition that different individuals may produce different allelic variants, or populations of allelic variants of keratin proteins in their skin. As used herein, the term "allelic variants" refers to different versions of a protein, or a gene encoding that protein, present in the human population. Protein variants can differ from one another by addition, substitution, or deletion of one or more amino acids. Typically, such proteins are produced from gene variants that differ from one another by addition, substitution, or deletion of one or more nucleotides. Alternatively or additionally, such protein variants can be produced by alternative splicing or other processing of genetic sequences.

According to one particularly preferred embodiment of the present invention, a particular individual is selected on the basis of having appealing hair characteristics. The allelic composition of one or more keratin proteins in that person's hair is identified, and that composition is reproduced in a hair treatment composition. Those of ordinary skill in the art will recognize that what constitutes "appealing" hair may vary according to the preferences of the manufacturer of the hair treatment composition or the person onto whom the hair treatment composition is to be used. For example, in some contexts, hair is "appealing" if it has attributes characteristic of the hair of a famous individual. In other contexts, hair may be "appealing" if it has certain desirable characteristics. Some non-limiting examples are smoothness, luster, tensile strength, flexibility, body, softness. Other non-limiting examples include hair characteristics as color, straightness, and curliness. In yet another context, hair is "appealing" if it has attributes similar or identical to those of the person to whom the hair treatment composition is to be applied so that the negative immune reactions can be minimized or avoided.

DETAILED DESCRIPTION OF THE PREFERRED EMBODIMENTS

Definitions

One aspect of the invention is a hair treatment composition containing a non naturally-occurring form of a hair keratin protein. The following definitions clarify the scope of this and other aspects of the invention:

The terms "formula", "hair treatment formula" or "hair treatment composition" as used herein, are intended to include any type of product that is applied in any manner directly to the person.

The terms "hair keratin protein" or "keratin protein" refer to those macromolecules that constitute intermediate filaments in hair cells. The two main classes of keratin proteins are the keratin proteins referred to as hard keratins, comprising, for example, hair, nail and tongue, and those referred to as soft keratin proteins, comprising epithelial keratin proteins.

"Non naturally-occurring", when applied to the keratin proteins of the present invention means polypeptides that have not been previously cross-linked. Such keratin proteins can be produced by methods well known by those skilled in the art in (and described in more detail herein), for example, bacterial or eukaryotic host cells.

"Non-naturally-occurring", when applied to nucleotide sequences encoding the keratin proteins of the present invention means a portion of genomic nucleic acid, cDNA, or synthetic nucleic acid which, by virtue of its origin or manipulation: (i) is not associated with all of a nucleic acid with which it is associated in nature; (ii) is linked to a nucleic acid or other chemical moiety other than that to which it is linked in nature; or (iii) does not occur in nature.

One significant feature of the present hair treatment compositions is that the non naturally-occurring keratin proteins of the invention have not previously been cross-linked. By "not previously cross-linked", it is meant that the proteins of the hair treatment compositions:

a. have not been cross-linked inside a body to form intermediate filaments.

b. have not been cross-linked in vitro to form intermediate filaments. It will be noted that keratin proteins have the ability to self assemble into intermediate filaments in vitro.

The term "soluble" refers to solubility of the precursor in aqueous solutions, such as water.

As used herein, the term "allelic variant" refers to different versions of a protein, or a gene encoding that protein, present in the human population. Protein variants can differ from one another by addition, substitution, or deletion of one or more amino acids. Typically, such proteins are produced from gene variants that differ form one another by addition, substitution, or deletion of one or more nucleotides. Alternatively or additionally, such protein variants can be produced by alternative splicing or other processing of genetic sequences.

The term "recombinant" as used herein refers to protein prepared by expression in a host cell system in which that protein is not expressed in nature, and in which the protein does not become cross-linked. A variety of methods of producing recombinant proteins are well known in the art, involving, for example, expression of a particular gene in a host cell by introduction of exogenous DNA sequences into the cell or activation of the endogenous gene (U.S. Pat. No. 5,641,670).

According to the present invention, when referring to amino acid substitutions, an amino acid sequence is "functionally equivalent" compared with the known sequences of proteins if the amino acid sequence contains one or more amino acid residues within the sequence which can be substituted by another amino acid of a similar properties that acts in a functionally equivalent way to the original amino acid. Substitutes for an amino acid within the sequence may preferably be selected from other members of the class to which the amino acid belongs. The non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid.

Keratin Proteins and Polypeptides

As discussed above, the present invention provides hair treatment compositions formulated from non-naturally-occurring keratin proteins. These proteins may be derived from mammals such a cows, sheep or pigs. Preferably, however, the inventive compositions utilize human keratin proteins. Particularly preferred proteins used in the invention are the "hard" keratin proteins expressed in human hair.

Keratins represent the major structural components of the water-insoluble intermediate filament system in hair. Genes encoding type I and II keratins have been cloned and the protein sequences determined (Fink et al., Biochem. Biophys. Acta 1264:12–14, 1995; Rogers et al., *Differentiation*, V. 61, pp. 187–194, 1997; Winter et al., 1997 supra; Yu et al., supra). As with all intermediate filament subunit proteins, a common secondary structure is found: a highly-conserved, central, alpha-helical domain consisting of four coiled-coil segments and non-helical end-terminal domains of diverse sequences and lengths that determine the chain specificity of an individual hair keratin. Hair keratins generally range in molecular weight form 40–62 kD. There exists a high degree of amino acid conservation in hair keratins among various species (mouse, sheep and human) (Yu et al., supra). The most significant difference between the hair keratins and other keratins is the cysteine residue content, which averages 7.6% in human hair keratin as compared with only 2.9% in epidermal keratins. This reflects the increased utilization of disulfide bonding in hair keratins to produce a tougher, more durable structure (Yu et al., supra).

The keratin proteins utilized in the present invention may be prepared by any of a variety of available techniques, but it is important that the proteins do not go through a cross linking step that must be reversed to solubilize the proteins as discussed above. It is preferable to avoid cross linking of the proteins during keratin protein expression and purification.

In some preferred embodiments of the invention, the proteins are synthesized using available chemical synthetic methods. For example, inventive non-naturally occurring keratin proteins can be synthesized using an appropriate solid state synthetic procedure, (Steward and Young, *Solid Phase Peptide Synthesis*). Freemantle, San Francisco, Calif., 1968). A preferred method is the Merrifield process, (Merrifield, *Recent Prog. Hormone Res.*, 23:451, 1967).

Alternatively, the genes encoding the proteins can be isolated and the proteins prepared using recombinant procedures. "Recombinant procedures" can be defined as any method of protein preparation by expression in host cells in which the keratin proteins are not cross-linked. A variety of methods of producing recombinant proteins are well known in the art that involve expression of a particular gene in a host cell by introduction of exogenous DNA sequences into the cell or activation of the endogenous gene, (U.S. Pat. No. 5,641,670). "Recombinant procedures" can also be used in reference to methods of in vitro transcription and translation to prepare the keratin proteins.

Protocols for isolating genes that encode particular proteins generally involve isolating total messenger RNA from vertebrate tissues, such as human hair, animal hair, wool and feathers, or from cell lines likely to express the protein of interest. Encoded proteins can then be expressed in an appropriate expression system well known in the art. A particular advantage of using a recombinant expression system is that each protein subunit is expressed separately from its partner protein with which it heterodimerizes, and therefore is less likely to become cross-linked and lose solubility.

Typically, total RNA from a tissue or cells in culture is isolated using conventional methods. Subsequent isolation of mRNA is typically accomplished by oligo (dT) chromatography. Messenger RNA is size-fractionated by electrophoresis and the RNA transcripts are transferred to, for example, nitrocellulose according to standard protocols (Sambrook, J. et al., *Molecular Cloning: A Laboratory Manual*, Cold Spring Harbor Press, N.Y., incorporated herein by reference). For example a labeled polymerase chain reaction (PCR)-generated probe capable of hybridizing with human keratin nucleotide sequences (Rogers et al., *Experimental Cell Research*, 220: 357–362, 1995) can serve to identify RNA transcripts complementary to at least a portion of the desired keratin protein gene. If Northern analysis indicates that RNA isolated from human scalp tissue with a labeled probe contains an allelic variant of keratin, then human scalp cells are utilized for preparation of a cDNA library to be screened for the desired gene.

Northern analysis can be used to confirm the presence in the library of mRNA fragments which hybridize to a probe corresponding to all or part of the relevant gene. Northern analysis reveals the presence and size of the transcript. This allows one to determine whether a given cDNA clone is long enough to encompass the entire transcript or whether it is necessary to obtain further clones in order to generate a full-length cDNA, i.e., if the length of the cDNA clone is less than the length of RNA transcripts as seen by Northern analysis. If the cDNA is not long enough, it is necessary to perform several steps such as: (i) re-screen the same library with the longest probes available to identify a longer cDNA; (ii) screen a different cDNA library with the longest probe; and (iii) prepare a primer-extended cDNA library using a specific nucleotide primer corresponding to a region close to, but not at, the most 5' available region. This nucleotide sequence is used to prime reverse transcription. The primer extended library is then screened with the probe corresponding to available sequences located 5' to the primer (see, for example, Rupp, et al, *Neuron,* 6:811, 1991).

The preferred clone utilized for expression has a complete coding sequence, i.e., one that begins with methionine, ends with a stop codon, and preferably has another in-frame stop codon 5' to the first methionine. It is also desirable to have a cDNA that includes all of the 5' and 3' untranslated sequences.

Of course, as will be appreciated by those of ordinary skill in the art, the above-described screening procedure is just one approach to isolation of genes to allow for recombinant expression of proteins. To name but one acceptable modification of the approach, an oligonucleotide probe may be employed instead of a PCR-generated probe to screen the library. An oligodeoxynucleotide probe typically has a sequence somewhat longer than that used for the PCR primers. A longer sequence is preferable for the probe, and it is important that codon degeneracy be minimized. A representative protocol for the preparation of an oligonucleotide probe for screening a cDNA library is described in Sambrook et al., *Molecular Cloning: A Laboratory Manual,* Cold Spring Harbor Press, New York 1989. In general the probe is labeled, for example with $^{32}$P, and used to screen clones of a cDNA or genomic library.

As another modification, the library need not be screened by hybridization at all, but rather can be prepared as an expression library that can be screened using conventional immunoassay techniques, such as those described in Harlow and Lane, D., *Antibodies,* Cold Spring Harbor Press, New York, 1988. Antibodies prepared using purified protein as an immunogen are preferably first tested for cross reactivity with the homolog of protein from other species.

In yet another version, a cDNA library is screened using the polymerase chain reaction (PCR). PCR screening permits the use of small samples for analysis. This technique depends upon the ability to amplify small amounts of hair mRNA or DNA using PCR and is based on procedures outlined in standard protocols. See, for example, Sambrook et al., supra. For example, a sample comprising as few as a thousand to as many as a hundred thousand specific mRNAs is extracted to release total RNA. The mRNA is converted to cDNA by using reverse transcriptase (See Example 2). The cDNA created is amplified in the same reaction mixture using PCR. Primers for the PCR reaction are preferably designed to hybridize to opposite ends of the relevant messenger RNA sequence, thus amplifying the entire mRNA segment.

To obtain maximum specificity and yield in PCR, one must adjust a variety of reaction parameters well known to those of ordinary skill in the art. (See for example McPherson, "PCR: A Practical Approach", Oxford University Press, New York, 1991) The primers should have 40–60% G+C content, no long stretches of any one base, and no interprimer complementarily longer than two bases, especially at the 3' ends. Given these conditions, the following steps may increase the specificity of PCR: the reaction can be run with primer, template, and dNTP concentrations in the middle of the recommended range, using 2.5 units of Taq DNA polymerase, using an annealing temperature at least 10 degrees C. lower than optimal. If nonspecific products are observed, one may optimize the annealing temperature and adjust the primer and dNTP concentrations.

Recombinant methods for producing the particularly preferred, non-naturally occurring human keratin proteins of the invention are readily available. One method involves constructing a human cDNA library and screening it for keratin cDNAs. The resulting clones can be introduced into an expression vector system and proteins expressed and purified using standardized methods. See, for example, Ausubel et al., *Current Protocols in Molecular Biology*, Greene Publishing Associates, New York, V. 1&2, 1996 and Sambrook et al., supra. The recombinant proteins thus produced can be characterized by, for example, polyacrylamide gel electrophoresis (PAGE) analysis, and N-terminal sequencing.

In one particular preferred embodiment of the present invention, a human cDNA library either prepared from a selected individual as described below or purchased from a commercial source (e.g., Clontech, Palo Alto, Calif.) is screened to identify cDNAs encoding human keratin. Positive clones are subject to sequencing and can be characterized by restriction endonuclease digestion to isolate and re-screen the original cDNA library. Variations in sequence among identified cDNAs indicate the presence of allelic variants of the protein (see below).

However the gene of interest if isolated, proteins can be expressed in any desirable expression system, including in vivo or in vitro systems. Well known in vivo expression systems utilize prokaryotic and/or eukaryotic (i.e., yeast, human) cells. See for example, *Current Protocols in Molecular Biology*, pp. 16.0.1–16.21.9, supra; see also Gene Expression Technology, Volume 185, *Methods in Enzymology*, (ed. D. V. Goiddel), Academic Press Inc., 1990, incorporated herein by reference.

A large number of vectors have been constructed that contain powerful promoters that generate large amounts of mRNA complementary to cloned sequences of DNA introduced into the vector. For example, and not by way of limitation, expression of eukaryotic nucleotide sequence in *E. coli* may be accomplished using lac, trp, lamda, and recA promoters. See, for example, "Expression in *Escherichia coli*", Section II pp. 11–195, V. 185, *Methods in Enzymology*, supra; see also Hawley, D. K., and McClure, W. R., "Compilation and Analysis of *Escherichia coli* promoter DNA sequences", *Nucl. Acids Res.*, 11:4891, 1983, incorporated herein by reference. Expression of any desired keratin protein (including, for example, a human hair keratin) in a recombinant bacterial expression system can be readily accomplished.

Yeast cells suitable for expression of the proteins of the invention include the many strains of *Saccharomyces cerevisiae* as well as *Pichia pastoris*. See, "Heterologous Gene Expression in Yeast", Section IV, pp. 231–482, V. 185, *Methods in Enzymology*, supra, incorporated herein by reference. Moreover, a large number of vector-mammalian host systems known in the art may be used provided the keratin protein produced are not cross-linked in those cells. See, Sambrook et al., Volume III, supra and "Expression of Heterologous Genes in Mammalian Cells", Section V, pp. 485–596. V. 185. *Methods in Enzymology*, supra, incorporated herein by reference.

Suitable expression systems include those that transiently or stably expressed DNA and those that involve viral expression vectors derived from simian virus 40 (SV40), retroviruses, and baculoviruses. These vectors usually supply a promoter and other elements such as enhancers, splice acceptor and/or donor sequences, and polyadenylation signals. Whichever expression system is chosen, is important that none of the host cells used produce cross linked keratin proteins. Possible vectors include, but are not limited to, cosmids, plasmids or modified viruses, but the vector system must be compatible with the host cell used. Viral vectors include, but are not limited to, vaccinia virus, or lambda derivatives. Plasmids include, but are not limited to pBR322, pUC, or Bluescript$^R$ (Stratagene) plasmid derivatives. Recombinant molecules can be introduced into host cells, for example, via transformation, transfection, infection, eletroporation, lipofection, etc. (See *Current Protocols in Molecular Biology*, pp. 9.0.1–9.17.3, supra) Generally, introduction of protein molecules into a host is accomplished using a vector containing protein DNA under control of regulatory regions of the DNA that function in the host cell. Expression can alternatively be accomplished by activation of the endogenous keratin gene. (See, for example, U.S. Pat. No. 5,641,670)

A wide selection of expression systems are commercially available and encompass many possible vectors and host cells. Certain preferred expression systems provide for overproduction of recombinant keratin protein. See for example, the overproduction methods described in U.S. Pat. No. 4,820,642 (Edman et al. Apr. 11, 1989), incorporated herein by reference. See also, *Current Protocols in Molecular Biology*, pp. 16.0.1–16.21.9, supra.

Once the recombinant proteins or polypeptides of the present invention are expressed, they may be isolated and purified by standard methods including chromatography (e.g., ion exchange, affinity, and sizing column chromatography), centrifugation, differential solubility, or by any other standard technique for the purification of proteins. See, for example, Scopes, "Protein Purification; Principles and Practice", 2 nd edition, Springer-Verlag, New York, 1987, incorporated herein by reference. For immunoaffinity chromatography in particular, a keratin protein of the invention encoded by human nucleotide sequences may be isolated by binding it to an affinity column comprising antibodies that were raised against that protein, and were affixed to a stationary support. Alternatively, affinity tags such as influenza coat sequence, and glutathione-S-transferase can be attached to the proteins of the invention to allow easy purification by passage over an appropriate affinity column.

Fragments

The hair treatment compositions of the present invention may utilize full-length proteins or alternatively may employ protein fragments. Fragments may be generated, for example, through expression of only partial coding sequences, or they may be generated directly from the intact protein.

Proteins are specifically cleaved by proteolytic enzymes, including, but not limited to, trypsin, chymotrypsin or pepsin. Each of these enzymes is specific for the type of peptide bond it attacks. Trypsin catalyzes the hydrolysis of peptide bonds whose carbonyl group is from a basic amino acid, usually arginine or lysine. Pepsin and chymotrypsin catalyze the hydrolysis of peptide bonds from aromatic amino acids, particularly tryptophan, tyrosine and phenylalanine. Alternate sets of cleaved polypeptide fragments are generated by preventing cleavage at a site which is susceptible to a proteolytic enzyme. For example, reaction of the, -amino groups of lysine with ethyltrifluorothioacetate in mildly basic solution yields a blocked amino acid residue whose adjacent peptide bond is no longer susceptible to hydrolysis by trypsin. Goldberger et al. *Biochem.*, 1:401, 1962. Treatment of such a polypeptide with trypsin thus cleaves only at the arginyl residues.

One preferred modification (see below) of keratin proteins (or genes encoding keratin protein) according to the present invention is therefore to render the proteins susceptible to proteolytic enzyme catalyzed hydrolysis. For example, alkylation of cysteine residues with &-halo ethylamines yields peptide linkages that are hydrolyzed by trypsin. Lindley, *Nature,* 178:647, 1956. In addition, chemical reagents that cleave polypeptide chains at specific residues can be used. Withcop, *Adv. Protein Chem.* 16:221, 1961. For example, cyanogen bromide cleaves polypeptides at methionine residues. Gross et al., *J. Am Chem Soc.,* 83:1510, 1961. Thus, by treating the proteins of the invention with various combinations of modifiers, proteolytic enzymes and/or chemical reagents, numerous discrete overlapping peptides of varying sizes are generated. These peptide fragments can be isolated and purified from such digests by chromatographic methods.

Modifications

In certain preferred embodiments of the present invention, the non-naturally occurring keratin proteins utilized in the inventive hair treatment compositions include a moiety designed to improve or enhance the protein's function. For example, the proteins of the present invention can be linked to a moiety that: (i) enhances the hair penetration capabilities of the protein; (ii) enhances the water or oil solubility of the protein; and/or (iii) enhances the ability of the protein to act as a surfactant. These additional moieties may be present in the naturally occurring (i.e., native) protein. Nevertheless, if they are present in the native protein, the additional moieties: (i) are linked to the present, non-naturally occurring keratin proteins of the invention at a different position than they are in the native protein; and/or (ii) are present in the non-naturally occurring keratin proteins of the invention in amounts that differ from those that are in the native protein.

These additional moieties can include a variety of substances and chemical compounds, including, but not limited to liposomes, fatty acids, carbohydrates, lipids, proteins and the like. The most preferred moieties are peptide sequences. The additional sequences can be located at any position in the protein chain. Preferably, they are located at the amino-terminal end of the protein, the carboxyl-terminal end of the protein, or both amino and carboxyl-termini.

Additional moieties may be introduced into the protein by linkage of a nucleotide sequence encoding the moiety with a nucleotide sequence encoding the protein, to result in expression of fusion proteins. Such fusion proteins contain the keratin protein with a specific desirable amino acid moiety attached to facilitate, for example, expression or purification of the keratin protein.

As but one example, additional nucleotide sequences encoding amino acid sequence moieties selected from the group consisting of hydrophilic amino acid sequences, hydrophobic amino acid sequences, cysteine-rich amino acid sequences, and combinations of the foregoing sequences may be linked to keratin encoding nucleotide sequences. The additional nucleotide sequences may be linked so that the keratin protein of the invention, when expressed in a suitable expression system, contains the additional amino acid moieties either: (i) internally; (ii) at the amino-terminus, the carboxyl-terminus, and/or both amino and carboxyl-termini of the protein.

In particular, preferred additional nucleotide sequences that introduce amino-terminal amino acids may have the formula (I):

$$\text{ATG-(NNN)}_x\text{—;} \qquad (I)$$

where A=adenylic acid, T=thymidylic acid, and G=guanylic acid, all joined to each other by phosphodiester bonds;

where x=1 to 20;

where N=a nucleotide base, such as for example, adenine, thymine, cytosine, guanine, uracil;

where $(NNN)_x$=a plurality of codons.

The term "N", can also include modified bases such as, but not limited to, 4-acetyl cytidine, 5-(carboxyhydroxymethyl)uridine, 2'-O-methylcytidine, dihydrouridine, the methylpseudouridines, inosine, 1-methyl adenosine, 1-methyl guanosine, N6-methyl adenosine, and others.

Nucleotide sequences of this formula may be linked to the nucleotide sequence of a keratin protein of the invention so that the amino-terminal end of the encoded protein contains a hydrophobic amino acid sequence moiety having amino acids selected from the group consisting of, for example, phenylalanine (encoded by the triplets UUU and UUC), tryptophan (encoded by the triplet UGG), proline (encoded by the triplets CCU, CCC, CCA, and CCG), glycine (encoded by the triplets GGU, GGC, GGA, and GGG), valine (encoded by the triplets GUU, GUC, GUA, and GUG) and combinations of the foregoing amino acids. Likewise, additional nucleotide sequences encoding for amino acids that are to be linked at the amino-terminus can also encode hydrophilic amino acid sequence moieties having amino acids selected from the group consisting of, for example, aspartic acid (encoded by the triplets GAU and GAC), glutamic acid (encoded by the triplets GAA and GAG), and combinations of the foregoing amino acids. Further, nucleotide sequences can include lysine-rich amino acid sequence moieties (encoded by the triplets AAA and AAG). The term "lysine-rich" means amino acid sequences containing at least 30 percent lysine residues.

Alternative or additional added nucleotide sequences may encode amino acid moieties that can be linked at the carboxyl-terminus of the keratin protein. In this case, the added nucleotides have the formula (II):

$$\text{—(NNN)}_x\text{-TGA;} \qquad (II)$$

where A=adenylic acid, T=thymidylic acid, and G=guanylic acid, all joined to each other by phosphodiester bonds;

where x=1 to 20;

where N=a nucleotide base, such as for example, adenine, thymine, cytosine, guanine, uracil;

where $(NNN)_x$=a plurality of codons.

The term "N", can also include modified bases such as, but not limited to, 4-acetylcytidine, 5-(carboxyhydroxymethyl)uridine, 2'-O-methylcytidine, dihydrouridine, the methylpseudouridines, inosine, 1-methyl adenosine, 1-methyl guanosine, N6-methyl adenosine, and others.

The codons can encode a hydrophobic amino acid sequence moiety having amino acids selected from the group consisting of, for example, phenylalanine, tryptophan, proline, glycine, valine, and combinations of the foregoing amino acids. Likewise, hydrophilic and lysine-rich amino acid moieties can be added at the carboxyl-terminus of the protein of the invention, using nucleotides encoding amino acid sequences as described above. Hydrophobic amino acid sequences tend to increase the lipid solubility of the protein of the invention. Hydrophilic amino acids serve to increase the water solubility of the protein. Cysteine-rich amino acid sequences enhance the cross-linking of the keratin protein.

Positioning sequence moieties at both the amino and carboxyl-termini of the proteins of the invention may enhance the amphipathic properties of the keratin protein. "Amphipathic" refers to a molecule that has both hydrophilic and hydrophobic groups. Amphipathic molecules are typically good emulsifiers (i.e., they can disperse one liquid into a second, immiscible liquid) and surfactants (i.e., they can reduce the surface tension of liquids or reduce interfacial tension between two liquids or a liquid and a solid).

Additional moieties may also be introduced into the proteins of the invention by conjugating the moieties to the expressed keratin protein using a variety of well-characterized linker molecules. Those of ordinary skill in the art will recognize that a large variety of possible linkers can be used with the proteins of the invention. See, for example, *Contributions to Microbiology and Immunology*, J. M. Cruse and R. E. Lewis, Jr (eds). Carger Press, New York, (1989), the entire contents of which are incorporated herein by reference. The conjugation of the proteins of the invention to another moiety (e.g. hydrophilic amino acid sequences) can be accomplished by any chemical reaction that will bind the two molecules so long as both molecules retain their respective activity. This linkage can include many chemical mechanisms, for instance covalent binding, affinity binding, intercalation, coordinate binding and complexation.

The preferred binding is, however, covalent binding. The covalent binding can be achieved either by direct condensation of existing side chains or by the incorporation of external bridging molecules. Many bivalent or polyvalent linking agents are useful in coupling protein molecules to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen et al., *J. Immunol.* 133:1335, 1984; Jansen et al., *Immuno. Rev.* 62:185, 1982; and Vitetta et al., supra).

Preferred linkers for coupling a moiety to the proteins of the invention are described in the literature. See, for example, Ramakrishnan et al., *Cancer Res.* 44:201, 1984 describing use of MBS (M-maleimidobenzoyl-N-hydroxysuccinimide ester). See also, Umemoto et al. U.S. Pat. No. 5,030,719, describing use of a halogenated acetyl hydrazide derivative coupled to an antibody by way of an oligopeptide linker. Particularly preferred linkers include: (i) EDC (1-ethyl-3-(3-dimethyl amino-propyl)carbodiimide hydrochloride (see Example 4); (ii) SMPT (4-succinimidyloxycarbonyl-alpha-methyl-alpha-(2-pyridyl-dithio)-toluene (Pierce Chem. Co., Cat. #21558G); (iii) SPDP (succinimidyl-6[3-(2-pyridyldithio) propionamido]hexanoate (Pierce Chem. Co., Cat #21651G); (iv) Sulfo-LC-SPDP (sulfosuccinimidyl 6[3-(2-pyridyldithio)propianamide]hexanoate (Pierce Chem. Co. Cat. #21650G); and (v) sulfo-NHS (N-hydroxy sulfo-succinimide: Pierce Chem. Co., Cat. #24510) conjugated to EDC.

The linkers described above contain components that have different attributes, thus leading to molecules with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form molecules with increased stability. Disulfide linkages, are in general, less stable than other linkages because the disulfide linkage is cleaved in vivo, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodiimide coupling reaction alone.

Modification of the keratin proteins for use in the present invention can be achieved by exploiting in vivo processing activity of a host or by in vitro chemical means, e.g., by phosphorylation, glycosylation, cross linking, acylation, proteolytic cleavage, linkage to an antibody molecule, membrane molecule or other ligand (Ferguson et al., *Ann. Rev. Biochem.* 57:285, 1988).

In addition, the nucleic acid sequences encoding proteins of the invention may be engineered so as to modify processing or expression. For example, and not by way of limitation, nucleotide sequence(s) encoding the non-naturally occurring keratin proteins may be combined with a promoter sequence and/or a ribosome binding site using well characterized methods, and thereby facilitate harvesting or bioavailability.

Additionally, a given nucleotide sequence can be mutated in vitro or in vivo, to create variations in coding regions and/or to form new restriction endonuclease sites or destroy preexisting ones, to facilitate further in vitro modification. Any technique for mutagenesis known in the art can be used including, but not limited to, in vitro site-directed mutagenesis (Hutchinson et al., *J. Biol. Chem.* 253:6551, 1978), use of TAB® linkers (Pharmacia), PCR-directed mutagenesis, and the like.

Certain preferred modifications to the keratin proteins utilized in accordance with the present invention include changes that reduce the likely antigenicity of the proteins. As noted above, the mere fact that the present invention utilizes soluble proteins already reduces the likelihood that these proteins will induce an immune response; alternately or additionally, the amino acid sequence of the non-naturally occurring keratin protein(s) intended to be used in the hair treatment compositions may be analyzed in order to identify portions of the molecule that may be associated with decreased immunogenicity.

For example, the amino acid sequence may be subjected to computer analysis to identify surface epitopes which present computer-generated plots of antigenic index, an amphophilic helix, amphophilic sheet, hydrophilicity, and the like.

Allelic Variants

As will be appreciated by those of ordinary skill in the art, multiple versions, or allelic variants, of the proteins can exist within populations. Such allelic variants differ from one another in the substitution, addition, or deletion of one or more amino acids. Often, these protein sequence differences reflect differences in the genomic sequence of the genetic alleles encoding the proteins. In other cases, the same genomic sequence encodes more than one allelic variant protein because of differences in RNA splicing, RNA editing, other RNA processing, or translational or post-translational events. For example, human Ha3 has two isoforms, Ha3-I and Ha3-II (Rogers et al., *Mol. Biol. Rep.,* 20:155–161, 1995).

One aspect of the present invention is the recognition that individuals within the population will express different collections of keratin protein allelic variants in their hair. Each individual might even have a unique constellation of such variants, the particular collection present in a given individual's hair can therefore be thought of as a "keratin fingerprint". In a preferred embodiment of the present invention, hair treatment compositions are formulated to re-create part or all of the keratin fingerprint of a selected individual (see below for further discussion).

It has been shown that keratin amino acid and cDNA sequence, including hair keratins, reveal considerable variability, likely due to point mutations or other sequence rearrangements, for example, nucleotide additions, deletions, and insertions. See, for example, Mischke et al., *The Journal of Investigative Dermatology,* V. 88, NO. 2, 2 February, pp. 191–197, 1987; and Winter et al., *The Journal of Investigative Dermatology,* V. 106, NO. 3, 2 March, pp. 544–548, 1996, incorporated herein by reference. Spontaneous mutations can occur for example, as a result of mistakes made by DNA polymerase during the process of DNA replication.

Protein allelic variants produced by alternative splicing are herein referred to as protein "isoforms" or "isomorphs". It is possible that some allelic variants are isoforms that result from alternative splicing although no such examples have yet been identified. Briefly, most eukaryotic DNA protein coding genes contain sequences present in the corresponding mature mRNA in discontinuous genomic DNA segments (exons) interspersed among sequences (introns) that do not form a part of the mature mRNA. These intron sequences are precisely excised by a multistep process. The majority of instances studied so far, each and every one of the exons present in a gene are incorporated into one mature mRNA through the invariant ligation of consecutive pairs of donor and acceptor splice sites, removing every intron. This type of "constitutive" splicing yields a single gene product from each transcriptional unit even when its coding sequence is split into many exons.

There are instances, however, in which nonconsecutive exons are joined in the processing of some, but not all, transcripts from a single gene. This "alternative" pattern of splicing can exclude individual exon sequences from the mature mRNA in some transcripts but include them in others. The use of such alternative splicing patterns in transcripts from a single gene yields mRNA's with different primary structures. When the exons involved contain translated sequences, these alternatively spliced mRNA's will encode related but distinct proteins, hereinafter referred to as "isomorphs". The capacity to generate different, but closely related protein isomorphs by alternative splicing increases significantly the phenotypic variability that can be obtained from single genes such as keratin.

The consequences of mutations in the DNA encoding structural keratin proteins are significant. For example, monilethrix is a rare autosomal dominant hair defect. Hairs from affected individuals show a structure resembling a string of beads. This hair defect is caused by an amino acid substitution of a conserved glutamic acid residue by a lysine or arginine residue at position 410 in the helix termination motif of the type II hair keratin hHb6 (Winter et al,. *Hum Genet,* December; 101 (2):165–169, 1997; and Winter et al., *Nat Genet,* August; 16(4):372–374, 1997). A second point mutation was identified in individuals affected with monilethrix, that substitutes glutamic acid residue 403, in the type II hair keratin hHb1, with a lysine residue (Winter et al., supra). Both hHb1 and hHb6 are coexpressed in the cortex of the hair shaft. This indicates that monilethrix is a disease of the hair cortex and demonstrates that small changes in the DNA sequence encoding hair keratin proteins can have a severe affect on the external appearance of hair.

In light of the above example, it is possible that the different allelic variants of keratin proteins, based upon differences in the coding regions of keratin messenger RNA, will also have altered biological properties. We note that an important feature that distinguishes the hair keratins from the soft keratins is that the terminal domains of hair keratins contain a different number of cysteine residues per molecule than the soft keratins. As the terminal domains are on the surface of the formed filament, most of these cysteine residues are considered to be involved in the formation of intermolecular disulfide bonds between keratin and either another keratin or matrix molecules. Thus, covalent intermolecular cross-links between keratin polypeptides may be affected by mutations affecting conserved cysteine residues.

Preparation of allelic variants of keratin proteins is relatively straightforward, once the message encoding the protein has been isolated. For example, once the known keratin messenger RNA has been amplified by the PCR method, one or more forms of the keratin messenger RNA sequence are present in sufficient quantity for analysis. The addition, deletion or substitution of any nucleotide(s) in the amplified sequence can be determined by cloning the amplified cDNA and determining the actual nucleotide sequence of the cloned gene.

Alternately, the presence or absence of any particular exon in the amplified sequence can be determined by preparing a series of probes of DNA based on known exon sequences (see Table 3 and references cited therein). The amplified DNA can be probed by hybridization for the presence or absence of each exon without directly sequencing the DNA. This method is generally preferable to the method described immediately above, for identifying isomorphic forms of keratin proteins, in that it is less time consuming and expensive. The DNA hybridization probes identify any missing exons and describe the sequence of the messenger RNA accurately enough so that it can be constructed in an expression system for eventual expression of that precise keratin isomorph.

Preparation of non-isomorphic allelic variants is equally straightforward in light of the teachings herein. When differences in protein sequence reflect differences in genomic DNA, pre-mRNA, mRNA, and/or edited or processed nucleic acids, the variants can be prepared as described above, through production of a cDNA library from the cells in which the variants are naturally produced.

When differences in protein sequence do not reflect nucleic acid sequence differences, they can nonetheless be identified by isolation of protein from cells in which the variant proteins are produced. The isolated proteins can then be subjected to any of a variety of analytical methods, including but not limited to immunological assays such as Western Blots or other binding studies, fragmentation studies, protein sequencing, etc. as is known in the art so that the precise chemical structure of the variants is determined.

Once the chemical structure is known, cDNAs encoding that structure can be prepared (e.g., synthetically, through PCR, or using recombinant DNA technology) to allow easy preparation of large amounts of each individual variant.

It will be appreciated that analysis of proteins present in hair of an individual will necessarily involve analysis of the processed, cross linked, insoluble forms of those proteins. The information gleaned from such analysis, however, allows preparation of analogous soluble proteins as described herein.

In certain preferred embodiments of the invention, hair treatment compositions are formulated to contain more than one allelic variant of the same protein; other preferred embodiments contain two or more different proteins, each of which may be present in more than one allelic forms. In especially preferred embodiments, the particular proteins and allelic variants are selected, and the composition is formulated, to reproduce the relative amounts of the proteins and/or allelic variants present in the hair of a selected individual (see below).

Preferably, an individual whose hair characteristics are intended to be emulated is selected, the relative amounts of one or more keratin proteins or allelic variants are determined as described herein, each keratin protein or allelic variant is then produced separately, preferably either synthetically or by expression of an engineered gene in a host cell, and the separately-produced proteins and/or variants, which have never been cross-linked, are recombined together in ratios approximating those at which they are observed in the hair of the selected individual. Most preferably, the individual is a human.

Functional Equivalents

Hair treatment compositions of the present invention containing non-naturally occurring keratin proteins include, but are not limited to, those containing the primary amino acid sequence of keratin, protein allelic variants thereof, and the like. The non-naturally occurring keratin proteins may include altered sequences in which functionally equivalent amino acid residues are substituted for residues within the sequence, resulting in a silent change.

According to the present invention, an amino acid sequence is "functionally equivalent", compared with the known sequences of proteins, if the amino acid sequence contains one or more amino acid residues within the sequence which can be substituted by another amino acid of a similar properties which acts in a functionally equivalent way to the original amino acid. Substitutes for an amino acid within the sequence may be selected from other members of the class to which the amino acid belongs. The non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid.

Substitutions are chosen for their effect on: (i) maintaining the structure of the peptide backbone in the area of the substitution, for example, as a sheet or helical conformation; (ii) maintaining the charge or hydrophobicity of the molecule; or (iii) maintaining the bulk of the side chain. The substitutions that in general are expected to induce greater changes, and that should be avoided, are those in which: (a) glycine and/or proline is substituted by another amino acid or is deleted or inserted; (b) a hydrophilic residue, e.g., ceryl or threonyl, is substituted for (or by) a hydrophobic residue, e.g., leucyl, isoleucyl, phenyl alanyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl, or (e) a residue having a bulky side chain, e.g., phenylalanine, is substituted for one (or by) one not having such a side chain, e.g., glycine.

Most deletions and insertions in the proteins, however, are not expected to produce radical changes in the characteristics of the protein. Nevertheless, when it is difficult to predict the exact effect of the substitution, deletion, or insertion in advance of doing so, one skilled in the art will appreciate that the effect will be evaluated using routine screening assays as described herein.

Selection criteria

Several of the selection criteria desirably used to formulate the hair treatment composition of the present invention have already been discussed, and will vary based upon the intended use of the hair treatment formula.

The present invention provides methods of formulating hair treatment compositions that mimic the keratin protein composition of an individual having certain desirable hair characteristics. For example, it is well known in the hair treatment products industry that users of hair treatments products desire to have appealing hair. In one particularly preferred embodiment of the present invention, the hair of human subjects is visually screened to select those subjects having the most appealing hair. One or more, preferably at least two, keratin protein allelic variants are then identified as being produced by the subject's cells, and a hair treatment composition containing soluble forms of these allelic variants is prepared as described herein.

Those of ordinary skill in the art will recognize that there is no universally accepted standard of what constitutes "appealing hair". Generally, when a reasonable person would consider a subject's hair to have aspects that typically characterize appealing hair (e.g., smoothness, luster, flexibility, body, and softness) the subject is considered to have appealing hair. However, the present invention provides for the preferences of individual hair treatment composition user's or manufacturer's to be taken into account. A "designer cosmetic" can be formulated as described herein to reproduce one or more aspects of the keratin protein composition of any individual. The user or formulator may select any person, on any basis, (e.g., a famous individual or an individual with particularly desirable hair characteristics), whose keratin composition is to be imitated. Preferred hair treatment compositions of the present invention can therefore be considered "recombinant hair treatment compositions" and provide hair treatment preparations tailored to the individual subject.

Formulations

Keratin protein according to the present invention can be added to any of a variety of hair treatment compositions. A wide variety of hair treatment compositions are available in the art (See Example 1).

In one embodiment, the keratin of the present invention is added to a hair cleansing composition such as a pre-shampoo, a shampoo or a conditioning rinse. In another embodiment the non-naturally occurring keratin of the present invention is added to a hair styling or shaping composition, for example, a gel, spray or mousse. In an alternative embodiment, the keratin described herein is added to a pre- or post-perm composition for the purpose of setting hair. In yet another embodiment, the composition of the present invention is used in hair bleaching, dying or tinting compositions.

In another aspect, the keratin of the present invention can be added to nail care products. It is known that finger nails and toe nails have a high percentage of keratin protein and thus fall within the scope of the present invention. For example, keratin protein may be added to nail polish or nail polish remover.

These hair and nail treatment compositions are not inclusive of all compositions to which keratin protein of the present invention may be added and is not meant to limit the scope of the invention described herein. It will be appreciated by those skilled in the art that non-naturally occurring keratin, according to the present invention can be added to any hair or beauty treatment composition as long as the keratin has not been crosslinked.

Assays

Any of a variety of assays can desirably be performed on the hair treatment compositions of the present invention, or components thereof, to ensure that they meet relevant formulation criteria.

For example, keratin proteins utilized in the inventive compositions are preferably highly purified. The purity of the proteins contained with the cosmetics of the invention may be tested by purifying the proteins using conventional methods, such as SDS gel electrophoresis and arbitrarily setting a purity standard (e.g., 95% purity) that meets or exceeds that purity need to pass the conventional skin testing assays described herein.

The ability of the inventive hair treatment compositions to protect against UV radiation can also be assayed using known procedures. For example, one series of tests is carried out with rats in which a part of the skin of the back of the rat is depilated and then exposed to ultraviolet radiation. A mousse composition, for example as taught in Example 1, is applied to the exposed skin of the treated rats and to the unexposed skin of control rats. The skin of the animals treated is observed for scaling.

The ability of the hair treatment composition to alter characteristics of hair can be measured by a variety of methods. For example, treatment of human hair or wool with reducing agent used in permanent wave compositions always result in a loss in weight of the hair sample, but in the presence of keratin polypeptides there is a gain in weight, or, at the most a smaller loss in weight than when reducing agents are used alone without keratin peptides. (See U.S. Pat. No. 3,842,848) Therefore the weight of the hair sample before and after treatment with the hair treatment composition can be a measure of the ability of the hair treatment composition to change the characteristics of hair. The ability of the keratin material to coat and protect the hair samples can also be assessed by the sample maintaining a smooth, soft and silky feel, very similar to the samples before treatment with the reducing agent. There are various other methods available to evaluate the effect of a hair treatment composition on hair (see Example 5).

EXAMPLES

The present invention will now be illustrated by the following non-limiting examples in which all percentages are weight percentages.

Example 1

Preparation of Hair Treatment Compositions

The following are Examples of hair care compositions to which keratin protein of the present invention can be added. The Examples are given solely for the purposes of illustration and are not to be construed as limitations of the present invention as many variations of the hair treatment compositions are possible without departing from its spirit or scope.

(i) The following shampoo is adopted from U.S. Pat. No. 4,439,417, incorporated herein by reference, and is prepared:

| | |
|---|---|
| triethanolamine lauryl sulfate | 18% |
| decomposition derivative of keratin material | 2.0% |
| perfume | 0.3% |
| colorant | small amount |
| water | balance |

(ii) The following anionic shampoo is adopted from U.S. Pat. No. 4,444,749, incorporated herein by reference, and is prepared:

| | |
|---|---|
| sodium salt of technical grade lauryl ether sulphate (100% M.A.) | 7 g |
| polymer prepared as described below | 0.5 g |
| lauric acid momoethanolamide | 2 g |
| alkylamine of lanolic acids, sold under the tradename LANAMINE | 2 g |
| methyl p.oxybenzoate | 0.1 g |
| tetrasodium salt of ethylene diamine tetracetic acid | 0.05 g |
| lactic acid q.s.p. | pH = 7.15 |
| water q.s.p. | 100 g |

Into 250 cc of a 2% solution of N, N-dimethylethylenediamine in water there are introduced in small successive portions, and with vigorous stirring, 8.85 g of a 1:1 copolymer of vinyl methyl ether and maleic anhydride having a specific viscosity of 0.1 to 0.5 in a 1% solution of the resin in dimethyl formamide at 25° C., care being taken that each successive portion of the copolymer introduced only when the preceding portion has been completely dissolved in the amine solution. To the resulting viscous solution there is added a mixture of equal proportions of ethyl alcohol and ethyl acetate which precipitates a solid polymeric product.

This reaction product may be used as a softening agent by introducing it into a shampoo in a proportion of a 0.5%. The shampoo thus treated provides a lather which is particularly soft to the touch and imparts to the hair high gloss and suppleness.

The product of this example may also be employed as a thickening agent for cosmetics, preferably in a concentration of about 2% or as a hair softening agent at concentrations of 0.5–2% by weight.

(iii) The following amphoteric shampoo is adopted from U.S. Pat. No. 4,444,749, incorporated herein by reference, and is prepared:

| | |
|---|---|
| lauroylcyclormidinium-1-ethoxyethionic acid-2 ethionic acid, disodium salt, sold under the tradename Miranol C2M | 30 g |
| polymer prepared as described in (i) | 0.5 g |
| lactic acid q.s.p. | pH = 3.5 |
| water q.s.p. | 100 g |

(iv) The following silicone gum/particulate premix is adopted from U.S. Pat. No. 4,983,383, incorporated herein by reference, and is prepared:

| Premix A | |
|---|---|
| Dimethicone[1] | 80 |
| Octylacrylamide/Acrylate/Butylaminoethyl Methacrylate Copolymer Particulate[2] | 20 |
| Premix B | |
| cyclomethicone[3] | 50 |
| silicone resin[4] | 50 |

[1]High viscosity (>1,000,000 CSTK) silicone gum available from G. E. Silicones.
[2]AMPHOMER ® polymeric particulate (having an original particle size range of 75–200 microns available form National Starch.
[3]Cyclomethicone having a D5 structure available from G. E. Silicones.
[4]Available from G. E. Silicones.

Using a mixer such as a ribbon type blender, the premix A components are combined and mixed until dispersed and until the AMPHOMER particulate has been pulverized to particles having an average diameter of between 0.15 m and 2.0 m. Using a separate mixing vessel, the premix B components are mixed until homogeneous. Premix A and premix B are then combined at a ratio of 57% A to 43% B and mixed until homogeneous.

The premix solution is then diluted as follows using a mixing vessel with a high speed-torque agitation system. The premix solution is mixed with additional premix B at a ratio of 70.175% premix solution to 29.825 premix B until homogeneous. The premix solution formed is mixed with additional premix B at a ratio of 50% premix solution to 50% premix B until homogeneous. This silicone gum/particulate premix can be used to make a variety of hair care products as illustrated in the following examples.

In examples (v, vi, ix, and x) of the dimethicone gum is a high viscosity (>1,000,000 CSTK) silicone gum available from G.E. Silicones and the Octylacrylamide/Acrylate/Butylaminoethyl Methacrylate Copolymer Particulate is AMPHOMER polymeric particulate having an original particle size range of 75–250 microns available from National Starch which when dispersed in the silicone gum is pulverized such that the particle size range is reduced to from about 0.15 m to 2.0 m.

(v) The following non-aerosol hair tonic is adopted from U.S. Pat. No. 4,983,383, incorporated herein by reference, and is prepared:

Shampoo Examples

| Component | % A | % B |
|---|---|---|
| Ammonium Lauryl Sulfate | 13.5 | 13.5 |
| Ammonium Laureth Sulfate | 4.0 | 4.0 |
| Ammonium Xylene Sulfonate | 0.1 | 0.1 |
| Dimethicone Gum[2] | 0.16 | 0.80 |
| Octylacrylamide/Acrylate/Butyl Aminoethyl Methacrylate Copolymer particulate[2] | 0.04 | 0.20 |
| Silicone Resin[1,2] | 0.40 | 2.00 |
| Cyclomethicone[1,2] | 0.40 | 2.00 |
| Perfume | 1.20 | 1.20 |
| Preservative | 0.033 | 0.033 |
| Cocoamide MEA | 4.0 | 4.0 |
| Ethylene Glycol Distearate | 2.0 | 2.0 |
| Cetearyl Alcohol | 0.60 | 1.00 |
| Sodium Citrate | 0.05 | 0.05 |
| Citric Acid | 0.05 | 0.05 |
| Sodium Hydroxide | 0.01 | 0.01 |
| Sodium Chloride | 1.0 | 1.0 |
| Water | Q.S. | Q.S. |

[1]Supplied by G.E. Silicones
[2]These components are combined in a silicone premix, e.g., as described in (iv).

Shampoo Processing

Ammonium lauryl sulfate, citric acid, sodium citrate and sodium hyroxide are added to the distilled water at about 15° C. The mixture is heated to from 70° C. to 80° C. The cocamide MEA and glycol distearate are added at this point. The ammonium laureth-3 sulfate, cetearyl alcohol and silicone premix are blended at 70° C. to 90° C. This mixture is added to the batch following the glycol distearate. The preservative and fragrance are then added. The batch is mixed for 5 minutes, then milled under high shear using conventional milling apparatus and then cooled to room temperature (15° C. to 25° C.). Sodium chloride and ammonium xylene sulfonate are added for viscosity control as needed. The final compositions have a pH of from about 5.0 to about 6.0.

These compositions are used in the same way one would use a standard shampoo. The hair is then dried and styled in the usual way. When used in this way, the compositions provide hair with effective cleaning, conditioning and styling, as well as a look of increased volume.

(vi) The following conditioner is adopted from U.S. Pat. No. 4,983,383, incorporated herein by reference, and is prepared:

Conditioner Examples

| Component | % A | % B |
|---|---|---|
| Cyclomethicone[1,2] | 4.41 | 3.90 |
| Cetyl Alcohol | 1.0 | 1.0 |
| Quaternium 18 | 0.85 | 0.85 |
| Stearyl Alcohol | 0.75 | 0.75 |
| Hydroxyethyl Cellulose | 0.50 | 0.50 |
| Stearimidopropyl Dimethylamine | 0.50 | 0.50 |
| Ceteareth-20 | 0.35 | 0.35 |
| Glyceral Monstearate | 0.25 | 0.25 |
| Fragrance | 0.25 | 0.25 |
| Dimethicone Gum[2] | 0.10 | 0.40 |
| Silicone Resin[1,2] | 0.40 | 1.00 |
| Citric Acid | 0.13 | 0.13 |
| Dimethicone Copolyol | 0.10 | 0.10 |
| Octyl Acrylamide/Acrylate/Butyl Aminoethyl Methacrylate Copolymer particulate[2] | 0.04 | 0.10 |
| Preservative | 0.033 | 0.033 |
| Water | Q.S. | Q.S. |

[1]Supplied by G.E. Silicones
[2]These components are combined in a silicone premix, e.g., as described in (iv).

Conditioner Processing

Hydroxyethyl cellulose is added to the distilled water at a temperature of 15° C. to 40° C. This mixture is well-dispersed, then heated to a temperature of from 60° C. to 90° C. Materials 2 through 8 are added to the batch while the temperature is maintained in this range. The mixture is stirred for approximately 10 minutes, then cooled to approximately 50° C. The remaining materials are added at this temperature. The mixture is milled under high shear for approximately 2 minutes using a conventional milling apparatus, then cooled to room temperature. The finished compositions have a pH of from about 3.5 to about 4.5.

These compositions are used as one would use standard rinse-type conditioning products, i.e., after shampooing, the conditioner is applied to the hair, allowed to stay on the hair for at least about one minute, and then rinsed from the hair. The hair is then dried and styled in the usual way. When used in this way, these compositions provide hair with effective conditioning, styling and a look of increased volume.

(vii) The following lotion for setting hair is adopted from U.S. Pat. No. 4,444,749, incorporated herein by reference, and is prepared:

| | |
|---|---|
| polymer prepared as described in (i) | 5 g |
| hydroxyethyl-dimethyl-cetyl ammonium chloride | 1 g |
| perfume | 0.2 g |
| amino-methyl-propane-diol, q.s.p. for neutralization | |
| water, q.s.p. | 100 cc |

(viii) The following non-aerosol hair tonic is adopted from U.S. Pat. No. 4,983,383, incorporated herein by reference, and is prepared:

| | |
|---|---|
| PVP/VA copolymer | 2.00% |
| lauramine Oxide | 1.00% |
| cocamide DEA | 0.80% |
| carboner 956 | 0.20% |
| potassium hydroxide | to adjust pH to between 6 and 7 |
| premix from (iv) | 0.25% |
| fragrance | Q.S. |
| preservative | Q.S. |
| water | Q.S. |

A non-aerosol hair tonic spray product is prepared as follows The lauramide oxide is mixed with part of the water at a ratio of 4 to 1 with, for example, a ribbon type mixer until homogeneous. The cocamide DEA is added and mixed until homogeneous. The premix from (iv) is added and mixed until homogeneous.

The remainder of the water is put into a stainless steel mixing vessel. The Carbomer 956 is mixed into the water using, for example, a triblender or eductor mixer. Mixing is continued until the Carbomer is completely dissolved. The potassium hydroxide is added while mixing.

The premix is added while mixing until homogeneous. The PVP/VA is then added and mixing is continued until the batch is homogeneous. The preservative is added and mixing is continued until homogeneous. The perfume is added and mixing is continued for an additional 10 minutes. Once the batch is well-mixed homogenization of the batch is performed using conventional apparatus. The final product is an opaque liquid having a pH of about 6 and 7.

The hair tonic is sprayed onto damp hair and the hair is then styled/dried. The amount of tonic used will depend on the volume/hold benefits desired and the amount of hair being treated as well as the texture of the hair. Use of this product on the hair provides a look of increased hair volume. The feel of the hair is desirably soft and manageable, not stiff and sticky as is the result with most hair styling products. The hold of the style is long lasting as well.

(ix) The following mousse compositions are adopted from U.S. Pat. No. 4,983,383, incorporated herein by reference, and are prepared:

| | % | |
|---|---|---|
| Component | A | B |
| A-46 propellant[1] | 7.50 | 7.50 |
| PVP/VA Copolymer (50% active) | 1.00 | 2.50 |
| Lauramine Oxide | 1.00 | 1.00 |
| Cocamide DEA | 0.80 | 0.80 |
| Silicone Resin[2,3] | 0.15 | 0.40 |
| Dimethicone Gum[3] | 0.10 | 0.40 |
| Cyclomethicone[2,3] | 0.40 | 2.00 |
| Octyl Acrylamide/Acrylate/Butyl Aminoethyl Methyacrylate Copolymer particulate[3] | 0.04 | 0.80 |
| Preservative | Q.S. | Q.S. |
| Fragrance | Q.S. | Q.S. |
| Water | Q.S. | Q.S. |

[1]A mixture of propane (20%), isobutane (78%) and n-butane (2%)
[2]Supplied by G.E. Silicones
[3]These components are combined in a premix as in (iv).

The gel compositions of the present invention are prepared using the method outlined in (viii) for the hair tonic, except that the Carbomer 940 is substituted for the Carbomer 956 and the triethanolamine is added before the preservative and mixed in until homogeneous. These compositions have a pH of about 6 to 7.

These compositions are used in the same way as the mousse compositions of (ix). When used in this way, these gel compositions provide effective conditioning, styling and a look of increased volume to hair.

The aerosol mousses of the present invention are prepared by combining all ingredients except the aerosol propellant into a batch called the concentrate. This concentrate is made by combining with agitation all of the ingredients except for the preservative and the premix prepared as in (iv), and mixing until well dispersed. The preservative and premix are finally added and mixing continued until these are thoroughly dispersed. The resulting mixture is then homogenized using conventional apparatus. The resulting concentrate has a pH of from 6 to 7. Aerosol mousse cans are prepared by placing 135 grams of concentrate into 5 oz. aluminum epoxy lined cans, placing mousse valves on can tops, drawing a vacuum to evacuate can headspace (to remove air), and crimping the valves into place. The propellant (15 grams) is added by pressure filling through the valve stem.

These compositions are massaged into clean/damp hair and the hair is then dried and styled. The amount of mousse used will depend on the volume/hold benefits desired and the amount of hair being treated as well as the texture of the hair. When used this way, these mousse compositions provide effective conditioning, styling and a look of increased volume of hair.

(x) The following gel compositions are adopted from U.S. Pat. No. 4,983,383, incorporated by reference herein, and are prepared.

| Component | % A | B |
|---|---|---|
| PVP/VA Copolymer | 1.00 | 2.50 |
| Lauramine Oxide | 1.00 | 1.00 |
| Cocamide DEA | 0.80 | 0.80 |
| Carbomer 940 | 0.40 | 0.60 |
| Triethanolamine | 0.36 | 0.56 |
| Silicone Resin[1,2] | 0.15 | 0.20 |
| Dimethicone Gum[2] | 0.10 | 0.40 |
| Cyclomethicone[1,2] | 0.02 | 0.40 |
| Octyl Acrylamide/Acrylate/Butyl Aminoethyl Methyacrylate Copolymer particulate[2] | 0.01 | 0.10 |
| Preservative | Q.S. | Q.S. |
| Fragrance | Q.S. | Q.S. |
| Water | Q.S. | Q.S. |

[1]Supplied by G.E. Silicones
[2]These components are combined in a premix as in (iv).

(xi) The following non-aerosol silicone hairspray is adopted from U.S. Pat. No. 4,983,383, incorporated herein by reference, and is prepared:

| Component | Weight % |
|---|---|
| Ethanol (190 proof) | 87.439 |
| PVP/VA Copolymer (50/50) | 10.00 |
| Cyclomethicone[1] | 1.60 |
| Dimethicone copolyol | 0.50 |
| Amphomer[3] particulate | 0.05 |
| Tixogel VP[4] | 0.10 |
| Polydimethysiloxane gum[5] | 0.20 |
| Octyl Salicylate | 0.01 |
| Keratin AMino Acids | 0.001 |
| Fragrance | 0.10 |
| | 100% |

[1]Cyclomethicone having a D[5] structure available from G.E. Silicones
[2]FF400 Dimethicone Copolyol available from Dow Corning
[3]Octylacrylamide/Acrylate/Butyl Aminoethyl Methacrylate Copolymer having an original particle size (before milling) of 75-200 microns, available from National Starch
[4]Quaternium 18-Bentonite available from United Catalysts
[5]SE-30 Gum available from G.E. Silicones The Amphomer® particulate is first dispersed in the polydimethyl siloxane gum using a dough style mixer at low speed for about 4 hours. The Amphomer®/gum mixture is then added to the cyclomethicone and mixed until dissolved using a dough style mixer for about 8 hours. The dimethicone copolyol is added and the composition mixed using the dough style mixer until homogeneous. The Tixogel® is then added and mixed using the dough style mixer until homogeneous. Using a Tek Mar® mill the composition is slowly milled with the ethanol until homogeneous. Using conventional mixing the PVP/VA/copolymer is added. The octyl salicylate, keratin amino acids, and fragrance are mixed into the composition in that order. The resulting hairspray provides improved hair conditioning and volumizing benefits with a softer feeling hair hold. Substantially similar results are obtained when an equivalent amount of a quarternium-18-hectorite (for example, the material sold under the trade name Bentene-38® by NL Chemicals), a stearalkonium bentonite (for example, the material sold under the trade name Tixogel VZ® by United Catalysts), or a stearaldonium hectorite (for example, the material sold under the trade name Bentone-27® by NL Chemicals), is substituted for the Tixogel VP® clay.

(xii) The following aerosol silicone hairspray is adopted from U.S. Pat. No. 4,983,383, incorporated herein by reference, and is prepared:

Aerosol Silicone Hairspray

An aerosol silicone hairspray can be prepared by combining the composition of (iv) with a propellant, for example, A-31 propellant, which is an isobutane propellant available from Phillips Petroleum, Inc., at a ratio of 3 parts hairspray composition to 1 part propellant.

(xiii) The following hairspray composition is adopted from U.S. Pat. No. 4,983,383, incorporated herein by reference, and is prepared:

| Component | Weight % |
|---|---|
| Hairspray Composition | |
| SD40 Alcohol | 87.29 |
| Premix 1 | 8.3 |
| PVP/VA Copolymer | 10.00 |
| Dimethicone Copolyol[1] | 0.30 |
| Octyl Salicylate | 0.01 |
| Keratin AMino Acids | 0.001 |
| Perfume | 0.10 |
| | 100% |
| Premix 1 | |
| D5 Cyclomethicone[2] | 4.35 |
| Siloxane Resin[3] | 4.35 |
| Polydimethylsiloxane Gum[4] | 1.74 |
| Amphomer ®[5] | 0.43 |
| DRO Water | 10.87 |
| Lauramine Oxide | 43.48 |
| Cocamide DEA | 34.78 |
| | 100% |

[1]FF400 Dimethicone Copolyol, available from Dow Corning
[2]Cyclomethicone having a D5 structure, available from G.E. Silicones
[3]GE SR545, available from G.E. Silicones
[4]SE-76 gum, available from General Electric Co.
[5]Octylacrylamide/Acrylate/Butyl Aminoethyl Methacrylate Copolymer having an original particle size (before milling) of 75–200 microns, available from National Starch The Amphomer® is first dispersed into the Polydimethyl Siloxane Gum using a dough-style mixer at a low shear speed for about 4 hours. The Amphomer®/gum mixture is then added to the cyclomethicone and siloxane resin and mixed until dissolved using a dough style mixer for about 8 hours. The DRO water is added and mixed until homogeneous. The lauramine oxide is added and mixed until homogeneous. The cocamide DEA is then added and mixed until homogeneous. The SD 40 Alcohol is then milled with the above mixture until homogeneous. The PVP/VA polymer, dimethicone copolyol, octyl salicylate, keratin amino acids, and perfume are then each in turn mixed into the composition. The resulting hairspray provides improved hair conditioning and volumizing benefits with a softer feeling hair hold.

(xiv) The following nail polish remover is adopted from U.S. Pat. No. 5,173,288, incorporated herein by reference, and is prepared:

| | |
|---|---|
| acetone | 54.0% |
| isopropyl alcohol | 33.0% |
| water | 9.0% |
| hydrolysed animal keratin[1] | 0.1% |
| PPG-12-PEG-50 Lanolin | 2.5% |
| cocamidopropyl dimethylamine propionate[2] | 0.5% |
| aminomethylpropanol salt of isostearic hydrolysed collagen[3] | 0.1% |
| fragrance and color | 0.8% |

[1]Crotein ASK 10–15% solution in alcohol (ex Croda).
[2]EMCOL 1655 (ex Croda)
[3]CROTEIN AD (ex Croda)

Other examples of hair care products can be found in U.S. Pat. Nos. 4,495,173, 4,542,014 and 5,612,014.

Example 2

PCR Amplification of Hair Keratin cDNA

Oligonucleotides Used for Amplification

Oligonucleotides are synthesized on a Biosearch DNA synthesizer. Most of the primers are mRNA-specific primers. The 5' primers and 3' primers are designed to hybridize to opposite extremes of the particular elastin mRNA sequence.

Amplification Method

RNA is reverse transcribed into cDNA using conventional methods. Briefly, a 10-:1 reverse transcription reaction mixture containing 1:g of total cellular RNA, 1×PCR buffer (20 mM Tris HCl, pH 8.3, 50 mM KCl; 2.5 mM $MgCl_2$/100:g of bovine serum albumin per ml), 1 mM dithiothreitol, 0.5 mM dNTP, 10 units of RNasin (Promega Biotec), 0.1:g of oligo (dT) and 100 units of BRL Moloney murine leukemia virus reverse transcriptase (Bethesda Research Laboratories) is incubated at 37° C. for 60 min, heated to 95° C. for 5–10 min, and then quick-chilled on ice. PCR is performed at a final concentration of 1×PCR buffer/50:M dNTPs/0.1:M each 5' and 3' primers/1×10$^6$ cpm of [$^{32}$P]-end-labeled primer/1 unit of *Thermus aquaticus* DNA polymerase (Taq polymerase) (Perkin-Elmer/Cetus) in a total volume of 50:1. The mixture is overlaid with mineral oil and then amplified with the Perkin-Elmer Cetus thermal cycler. The amplification profile involves denaturation at 95° C. for 30 sec, primer annealing at 55° C. for 30 sec. and extension at 72° C. for 1 min.

Example 3

Construction and Screening of a Human Scalp cDNA Library

This method is adapted from Rogers et al., Differentiation, V. 61, pp. 187–194, 1997, and Rogers et al., *Experimental Cell* Research, V. 220, pp. 357–362, 1995, incorporated herein by reference.

Total mRNA is isolated from a 3-cm$^3$ piece of surgically removed human scalp (Winter et al., *Exp. Cell Res.*, V. 212, pp. 190–200, 1994) incorporated herein by reference. Five micrograms of poly(A)$^+$RNA is used to prepare a cDNA library in Lambda Zap II according to the manufacturer's instructions (cDNA Cloning Systems, Stratagene).

The library is screened with a 700-bp StyI/StyI fragment of the murine type I hair keratin mHa2 clone (see Winter et al., *Exp. Cell Res., pk V.* 212, pp. 190–200, 1994) which contains both sequences coding for an a-helical subdomain and the carboxyterminus as well as 3'-noncoding sequences. A second screen can be performed with a 570-bp StyI/PstI fragment of the murine type II hair keratin mHb4 clone (see Yu et al., *J. Invest. Dermatol.*, V. 97, pp. 354–363, 1991; and Tobiasch et al., *Mol. Biol. Rep.* V. 16, pp. 39–47, 1992) encompassing uniquely a-helix-coding sequences. The probes can be labeled by nick translation with a[$^{32}$P]dCTP.

Alternatively, screening probes can be synthesized by the polymerase chain reaction (PCR). A 182-bp segment of the region coding for the aminoterminus of the murine type-II hair keratin mHb4 (nucleotide positions 197–379) of clone MHKB2 (Yu et al., *J. Invest. Dermatol.*, V. 97, pp. 354–363, 1991) is amplified from mouse genomic DNA using the primers 5'CCTGCTACCGAGGACTCTCAGG-3' (forward primer; SEQ. ID No:1) and 5'-CGATCTCCAGGT TCAGGGGTGT-3' (reverse primer; SEQ. ID No:2). Similarly, a 284-bp segment of the region coding for the carboxyterminus and the 3'-noncoding region of a murine type II hair keratin clone pmKII-6 (see Tobiashch et al., *Mol. Biol. Rep.*, V. 16, pp., 39–47, 1992) is amplified using primers 5'-TGCAGCGGAAACGTGGTGG-3' (forward primer; SEQ. ID No:3) and 5'-CTGGGGCAG CGGATCCTCCAG-3' (reverse primer; SEQ. ID No:4). The amplified DNA fragment can be used as a probe to screen the human scalp cDNA library (as per Rogers et al., *Differentiation*, 61, 187–194, 1997). A human cosmid library, (for example pWE15: Clontech. Palo Alto. Calif.), can be screened with PCR-cloned hair keratin genomic DNA (ghHKb2-1) labeled by nick translation with g[$^{32}$P]-dCTP (see Bowden et al., *The Journal of Investigative Dermatology*, V. 110, NO. 2, February, 1998). Similar primers may be generated by those of ordinary skill in the art from known mRNA sequences of other proteins. Once the appropriate clones have been isolated, the keratin proteins may be expressed and purified.

The PCR is performed in 1× PCR buffer which is: 10 mM Tris-HCl, pH 8.85, 25 mM KCl, 5 mM $(NH_4)_2SO_4$, 2.0 mM $MgSO_4$, with 200 mM dNTP's, 50 pmol primer and 2.5 units Taq polymerase at 94° C. for 30 seconds; 56° C. for 40 seconds; 72° C. for 50 seconds, for 30 cycles. The PCR products are separated on a 3.5% low-melting agarose gel and purified by Gelase digestion (Biozym, Oldendorf, Germany) and ethanol precipitation.

However the probes are generated, the probes are used in a low-stringency plaque hybridization scheme (prehybridization and hybridization with 6× SSC, 0.1% SDS, 5× Denhardt's solution at 50° C. for 24 hours. Filters were washed 3× for 30 minutes with 2× SSC, 1% SDS at 55° C.) (Rogers et al., Exp. Cell Res., supra) incorporated herein by reference.

Characterization of Keratin cDNA's

Positive bacteriophage clones are purified and converted to Bluescript phagemids by automatic excision according to manufacturer's instructions (Stratagene) and sequenced from both ends. The partial sequences are analyzed using the EMBL Nucleotide Data Base to eliminate clones coding for known keratins (most likely epidermal keratins). Sequencing of the remaining possibly unique clones is performed by the dideoxy chain termination method, (see Sanger et al., *Proc. Natl. Acad. Sci. USA*, V. 75, pp. 5463–5467, 1977) initially using the universal M13 and T3 primers followed by 17-mer oligonucleotide walking primers specific to the newly cloned sequence.

Hybridization with Exon-specific Probes

Oligonucleotide sequences specific for individual exons are selected by methods described herein. The exon-specific oligonucleotides are synthesized using a modification of the phosphite method of Mateeucci (*J. Am. Chem. Soc.*, 103:3185, 1981) employing a MilliGen (Bedford, Mass.) programmable synthesizer. The synthetic oligonucleotides are purified by reverse phase high-pressure liquid chromatograph (Varian 5000).

Exon-specific synthetic oligonucleotides are radioactively labeled at the 5'-end, with ([$^{32}$P]dATP, by a phosphate exchange reaction catalyzed by T4 polynucleotide kinase. For elucidation of the presence or absence of a specific exon sequence within the identified human scalp clones, 100 ng of the insert cDNA is denatured, dotted onto nitrocellulose filters, and hybridized with 10 ng of the radiolabeled exon-specific oligonucleotide probe. Filter prehybridization is performed in a solution consisting of 0.9 M NaCl, 90 mM sodium citrate (pH 7.0), 0.5% sodium dodecylsulfate, 100 mg/ml denatured salmon sperm DNA, 0.1% polyvinyl pyrrolidine, 0.1% bovine serum albumin, and 0.1% Ficoll, at 42° C. for 2 h. The hybridization, following addition of the labeled synthetic oligonucleotide probe, is carried out for 16 hours in the same solution. The filters are washed at a final stringency of 0.15 M NaCl, 15 mM sodium citrate, at 55° C. for 60 min.

Example 4

Production of Recombinant Human Keratin

The following procedures are adopted from those of Manabe et al., *Biochemical and Biophysical Research Communications*, V. 229, pp. 965–973, 1996, incorporated herein by reference.
Construction of Expression Vector and Expression of Keratin Keratin cDNA, reverse transcribed from the mRNA of human scalp cells (see Example 3), is cloned into an expression vector, such as PECE. Preferably, full length cDNA of either the human acidic or basic hair keratin genes is inserted into the Eco RI cloning site of PECE under control of the SV40 early promoter. PtK2 cells (purchased form the American Type Culture Collection) and rat epidermal keratinocytes (Dr. Howard P. Baden of Harvard University Boston) are grown in DMEM (Gibco) supplemented with 10% fetal calf serum (Gibco). All cultures were grown in a 5% $CO_2$ atmosphere at 37° C. The transfections into PtK2 cells and rat epidermal keratinocytes are performed by the lipofection method using LipofectAMINE and LipofectACE reagent (Gibco), respectively, according to manufacuter's instructions.

To determine the presence and the state of the transfected proteins, cells are disrupted 48 hours after trasfection and an insoluble keratin pellet is obtained by sequential extraction in non-ionic detergent with low and high salt buffers (see Schweizer et al., *Exp. Cell. Res.* V. 184, pp. 193–206, 1993). The pellet is resuspended in sample buffer and separated by SDS-PAGE. Samples are then transferred to a nitrocellulose membrane using a Bio-Rad transfer apparatus, and the membranes are blocked by overnight incubation in MT buffer (5% non-fat dried milk, 0.2% Tween 20 in PBS for 2 hours at room temperature (see Schweizer et al., *Exp. Cell. Res.*, supra). The membrane is probed with antibodies to the desired keratin proteins (see for example, Westgate et al. Br. J. Dermatol., July, 197(1): 24–30, 1997). The presence of bound antibody is detected by incubation with biotinylated goat anti-mouse antiserum and avidin-peroxidase complex (SensiTek, Sytek) followed by subsequent development using enhanced chemiluminescence (ECL, Amersham) according to the manufacturer's recommendations.

Example 5

Assessment of Hair Characteristics (i) Hair properties can also be assessed by the following methods: (See U.S. Pat. No. 5,612,024)

a) Elongation measurements on treated hair

Alkinco type 6621 hair tresses (tress length: 12 cm) are used for measurement.

The tresses are treated for 20 minutes with the test shampoo, then rinsed for about 30 seconds and dried with a blow dryer for about 1.5 hours at 38° C. The tresses are then ultrableached for 20 minutes (composition of the ultrableach: 6% by weight of hydrogen peroxide, 15% by weight of ammonium peroxydisulfate, concentrated ammonia at pH 9.4, remainder water) and rinsed with water for about 1 minute. The wet tresses are then shampooed, rinsed and dried as described above. The tresses are then cold-waved (wave solution: 7% by weight thioglycolic acid, conc. ammonia at pH 9.0, remainder water), rinsed with water (38° C.) for about 1 minute and treated with a fixing solution (2% by weight hydrogen peroxide, citric acid at pH 4.0, remainder water), shampooed, rinsed and dried as described above. The cycle of ultrableaching, rinsing, shampooing, rinsing, drying, cold waving, rinsing, fixing, rinsing, shampooing, rinsing and drying is then repeated another two times. For the dry measurement, the tresses are heated in air at 38° C. For the wet measurements, the tresses are stored in water until just before the measurement. The following values can be determined:

Maximum breaking stress (tensile force at which the hair breaks)

15% Elongation value (tensile force at which the hair is elongated by 15%)

Breaking elongation (% elongation at which the hair breaks)

Brittleness

Particulars of the measuring process can be found in the literature (Ärztl. Kosmetologie 15, 347–355 (1985) and Parfumerie & Kosmetik 72, 74–81 (1991)).

Brittleness is determined as the percentage of hairs which show a break at 20% elongation and less.

b) Determination of the dry combing work

The dry combing work can be determined, for example, on brown hair, (Alkinco 6634, tress length 12 cm, tress weight 1 g) in the form of a comparison of paired mean values. To determine the zero value, the tresses are rinsed with water (1 l/min, 38° C.) for 1.5 minutes and combed out. The tresses are then dried with a blow dryer for 40 minutes at 45° C. After conditioning for 12 hours at 30° C./40% relative air humidity the combing work is determined. The tresses are treated with 100 g of the formulation for 5 minutes and then rinsed, dried and conditioned as described above. The dry combing work is then determined. Particulars of the measuring process can be found in the literature (Ärztl. Kosmetologie 20, 498–502 (1990)). Conditions are maintained so that no crosslinking of keratin proteins occurs during expression, possibly requiring the expression of a single keratin polypeptide in a single cell.

(ii) Evaluation method for pre-shampoo treatment: (See U.S. Pat. No. 4,495,173)

a) Feeling of hair during washing

Tresses made of hair of Japanese female with a length of 20 cm and a weight of 20 g are each applied with 2 g of each of pre-shampoo treatments. After allowing to stand for 5 minutes, the hair is applied with 2 g of a commercially available plain shampoo and lathered as usual for 1 minute, whereupon the feeling of the hair is evaluated. The evaluation is made by a paired comparison test in which a tress treated with a commercially available pre-shampoo hair treatment mainly composed of lanolin is used as a control.

b) Feeling of Hair in wet state

After the completion of the evaluation of the feeling of the hair during washing, it is washed with running water of 40° C. for 1 minute and dried with a towel to remove excess water. The tress is evaluated similarly to the tress during washing to know the feeling in a wet state.

c) Feeling and combing ease after drying

After the evaluation of (b), the wet hair tresses are each air dried and its feeling evaluated in accordance with the method of (b). Then the combing ease is evaluated similarly to the method of (a) using a commercially available nylon comb.

Equivalents

It should be understood that the preceding is merely a detailed description of certain preferred embodiments of the present invention. It therefore should be apparent to those skilled in the art that various modifications and equivalents can be made without departing from the spirit or scope of the invention.

What is claimed is:

1. A method of formulating a hair treatment composition, the method comprising steps of:

selecting a human individual on the basis of that individual having appealing hair characteristics obtaining at least one nucleic acid, each of which encodes a different keratin allelic variant that is present in hair of the human individual;

introducing each of the at least one obtained nucleic acids into an expression vector so that a population of expression constructs, each of which encodes at least one keratin allelic variant is produced;

introducing each expression construct into a host cell so that a population of host cells, each of which has received an individual expression construct and expresses a non-crosslinked keratin allelic variant therefrom, is produced;

identifying those host cells in the population of host cells that express one of the at least one keratin allelic variants in a manner that does not result in crosslinking of the at least one produced keratin allelic variants;

purifying each of the at least one keratin allelic variants from the host cell that produces them; and combining the purified keratin allelic variants with one another and also with components of a hair treatment composition to form a hair treatment composition.

2. The method of claim 1, wherein the step of obtaining comprises obtaining at least two nucleic acids.

3. The method of claim 1 or 2, wherein the step of obtaining comprises obtaining at least one nucleic acid, each of which encodes an allelic variant of a keratin protein selected from the group consisting of hHa1 hHa2, hHa3-I, hHa3-II, hHa4, hHa5, hHRa1, hHb1, hHb3, hHb5, hHb6, Hax, and Hbx.

4. In a method of formulating a hair treatment composition comprising keratin, the improvement that comprises:

selecting a particular human individual on the basis of that individual having appealing hair characteristics;

obtaining at least one nucleic acid, each of which encodes a different one of at least one keratin allelic variant that is naturally produced in hair of the selected human individual;

introducing each of the at least one nucleic acids into an expression vector;

introducing each of the expression vectors into its own host cell so that each of the at least one keratin allelic variants is recombinantly produced in a host cell;

purifying each of the recombinantly produced keratin allelic variants;

combining the purified keratin allelic variants with one another and also with a hair treatment composition.

5. The method of claim 4, wherein the step of introducing each of the at least one nucleic acids into an expression vector comprises introducing at least two nucleic acids.

6. The method of claim 1, 2, or 4 wherein the step of combining comprises combining at least two purified keratin allelic variants with one another in ratios approximating those at which they are found in tissue of the selected individual.

7. The method of claim 1, 2, or 4 wherein the step of providing comprises providing a human individual onto whom the hair treatment composition is to be applied.

8. The method of claim 1, 2, or 4 wherein the step of providing comprises providing a human individual other than one onto whom the hair treatment composition is to be applied.

9. The method of claim 1, 2, or 4 wherein the step of providing comprises providing a human individual whose hair characteristics appeal to an individual onto whom the hair treatment composition is to be applied.

10. The method of claim 1, 2, or 4 wherein the step of providing comprises providing a human individual on the basis of predetermined criteria established by the composition manufacturer.

11. The method of claim 1, 2, or 4 wherein the step of providing comprises providing a human individual on the basis of predetermined criteria established by the composition wearer.

12. The method of claim 1, 2, or 4 wherein the step of providing comprises providing a human individual on the basis of that individual being a wearer of the composition.

13. The method of claim 1, 2, or 4 wherein each of the at least one keratin allelic variant comprises a full-length keratin.

14. The method of claim 1, 2, or 4 wherein each of the at least one keratin allelic variant comprises a truncated keratin.

15. The method of claim 1, 2, or 4 wherein each of the at least one keratin allelic variant is selected from the group consisting of hydrolyzed keratins, full length keratins and truncated keratins.

16. The method of claim 1, 2, or 4 wherein the step of obtaining comprises steps of:

preparing a cDNA library from cells of the individual that express the allelic variants;

screening the cDNA library to identify at least one isolate containing a cloned sequence that encodes a keratin protein allelic variant.

17. The method of claim 1, 2, or 4 wherein the step of purifying comprises purifying each keratin allelic variant until it is at least about 95% pure.

18. The method of claim 1, 2, or 4 wherein the human individual is selected based on one or more characteristics of the hair of the individual selected from the group consisting of softness, smoothness, luster, tensile strength, flexibility, body, preferred color, straightness, curliness, and waviness.

19. A hair treatment composition comprising:

an aqueous solution of a detergent;

at least two keratin protein allelic variants, present in ratios approximately identical to those at which the variants are present in hair of an individual.

20. The hair treatment composition of claim 19 wherein at least one of the keratin protein allelic variants has been modified to increase its solubility.

21. The hair treatment composition of claim 20 wherein the modification comprises addition of a moiety selected from the group consisting of liposomes, fatty acids, carbohydrates, lipids, and proteins.

22. The hair treatment composition of claim 19 wherein at least one of the keratin protein allelic variants has been modified to reduce its antigenicity.

23. The hair treatment composition of claim 21 wherein the modification comprises addition of amino acids to a protein selected from the group consisting of hydrophobic amino acids, hydrophilic amino acids, and cysteine-rich amino acids.

24. The hair treatment composition of claim 22 wherein the modification comprises alteration of a solvent-accessible portion of the keratin protein allelic variant.

* * * * *

UNITED STATES PATENT AND TRADEMARK OFFICE
CERTIFICATE OF CORRECTION

PATENT NO. : 6,572,845 B2  Page 1 of 1
APPLICATION NO. : 09/174186
DATED : June 3, 2003
INVENTOR(S) : Burt D. Ensley It is certified that error appears in the above-identified patent and that said Letters Patent is hereby corrected as shown below:

Column 30
Lines 63-64, the phrase "selecting a human individual on the basis of that individual having appealing hair characteristics" is corrected to read --providing a human individual--.

Column 31
Lines 31-21, the phrase "selecting a particular human individual on the basis of that individual having appealing hair characteristics" is corrected to read --providing a particular human individual--.

Signed and Sealed this

Sixth Day of November, 2007

JON W. DUDAS
*Director of the United States Patent and Trademark Office*